United States Patent [19]
Eldridge et al.

[11] Patent Number: 5,716,408
[45] Date of Patent: Feb. 10, 1998

US005716408A

[54] PROSTHESIS FOR HERNIA REPAIR AND SOFT TISSUE RECONSTRUCTION

[75] Inventors: Stephen N. Eldridge, Cranston; Kelly M. Shriner, Barrington, both of R.I.; Ira M. Rutkow, Marlboro; Alan W. Robbins, Freehold, both of N.J.

[73] Assignee: C.R. Bard, Inc.

[21] Appl. No.: 656,554

[22] Filed: May 31, 1996

[51] Int. Cl.$^6$ .................................................. A61F 2/02
[52] U.S. Cl. .................................................. 623/11; 606/213
[58] Field of Search ........................... 623/11; 606/151, 606/213, 214, 215

[56] References Cited

U.S. PATENT DOCUMENTS

| | | | |
|---|---|---|---|
| 5,356,432 | 10/1994 | Rutkow | 623/11 |
| 5,370,650 | 12/1994 | Tovey | 623/11 |
| 5,397,331 | 3/1995 | Himpens | 623/11 |
| 5,433,996 | 7/1995 | Kranzler | 623/11 |

Primary Examiner—Michael J. Milano
Attorney, Agent, or Firm—Wolf, Greenfield & Sacks, P.C.

[57] ABSTRACT

An implantable prosthesis for repairing or reconstructing a tissue or muscle wall defect including an outer plug and at least two inner filler plugs positioned within the outer plug that stiffen, and impart bulk to, the outer plug when the implant is inserted into the narrow confines of the tissue or muscle wall defect.

20 Claims, 2 Drawing Sheets

PROSTHESIS FOR HERNIA REPAIR AND SOFT TISSUE RECONSTRUCTION

FIELD OF THE INVENTION

The present invention relates to an improved prosthesis for hernia repair and soft tissue reconstruction.

BACKGROUND OF THE INVENTION

The PerFix® Plug, available from C. R. Bard, Inc, the assignee of the present application, and described in U.S. Pat. No. 5,356,432, is a pre-formed, knitted polypropylene monofilament mesh prosthetic used in the repair of direct, indirect and femoral hernias. The PerFix® plug 10, illustrated in FIG. 1, consists of a hollow, conical outer body 12, that tapers outwardly from a rounded tip 14 to an open base 16. The surface of the outer body is pleated 18, allowing the implant to conform to irregularities in the tissue or muscle wall defining the defect. An inner filler body of mesh petals 20 is provided within the outer plug and imparts bulk, for handleability, and stiffness to snugly fit the prosthetic within the tunneling defect, preventing the formation of gaps between the implant and the surrounding muscle or tissue wall which may potentially lead to recurrent herniation. The atraumatic tip of the implant is inserted into the defect until the margin of the base is flush with the opening to the defect. The implant is secured in position with interrupted sutures through the mesh margin. The PerFix® plug has achieved notable commercial success and widespread recognition from the surgical community as a significant advance in the treatment of groinal hernia defects.

The present invention is an enhancement of the PerFix® plug, particularly indicated for use in the repair of large tissue ruptures.

SUMMARY OF INVENTION

The present invention is a biologically compatible, implantable prosthesis for use in the repair of groinal hernia defects and in other soft tissue reconstruction. The repair and reconstructive device includes an outer plug, preferably formed of a single layer of tissue infiltratable fabric, which is compressible into a slender shape which fits within an opening in a tissue or muscle wall defect. The surface of the outer plug may be pleated to facilitate conformance of the plug to irregularities in the shape of the rupture. An inner filler body, consisting of at least two plugs also preferably formed of single layers of a tissue infiltratable fabric, is positioned within the outer plug and imparts bulk to, and stiffens, the implant when it is compressed within the defect. Use of the inner filler plugs avoids the need to stiffen the single layer outer plug itself, reducing the likelihood that the prosthesis will kink or buckle when fitted in an irregularly shaped opening.

In one embodiment of the invention, the prosthetic includes a conical mesh outer plug having a rounded atraumatic tip, an open base and a cavity therebetween. Two or more similarly shaped, but smaller, conical filler plugs are fixedly positioned within the cavity with the tips of the mesh filler plugs being stitched to the tip of the larger outer plug. Sidewall stitches may be used to secure the inner filler plugs to the mesh outer plug, preventing the smaller plugs from riding up the sidewall of the outer plug and potentially obscuring the margin of the implant which is typically employed as a site for suturing the prosthetic to neighboring tissue. The outwardly resilient inner plugs fill the open space of the hollow outer plug, enhancing the bulkiness and stiffness of the implant when the outer conical plug is compressed upon insertion into the defect.

It is among the general objects of the invention to provide an implant for the repair of inguinal hernias and for other types of soft tissue reconstruction.

It is another object of the invention to provide a prosthesis which is particularly indicated for the treatment of large defects in muscle and tissue wall.

Other objects and features of the present invention will become apparent from the following detailed description when taken in connection with the accompanying drawings which disclose multiple embodiments of the invention. It is to be understood that the drawings are designed for the purpose of illustration only and are not intended as a definition of the limits of the invention.

DESCRIPTION OF THE DRAWINGS

The foregoing and other objects and advantages of the invention will be appreciated more fully from the following drawings in which.

DESCRIPTION OF THE PREFERRED EMBODIMENTS

Figure 1:
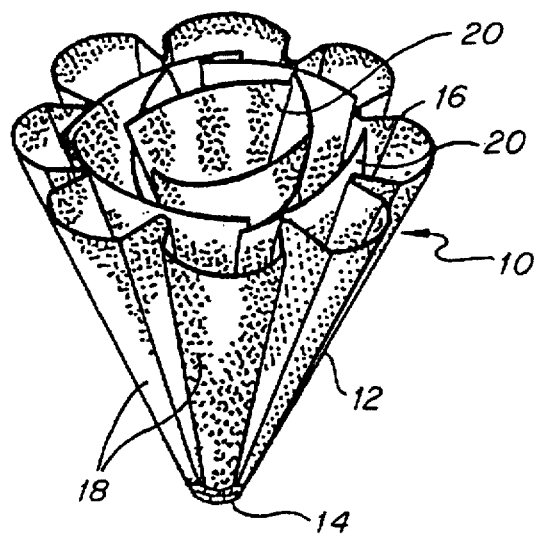
FIG. 1 is an illustration of the PerFix® plug disclosed in U.S. Pat. No. 5,356,432.
Figure 2:
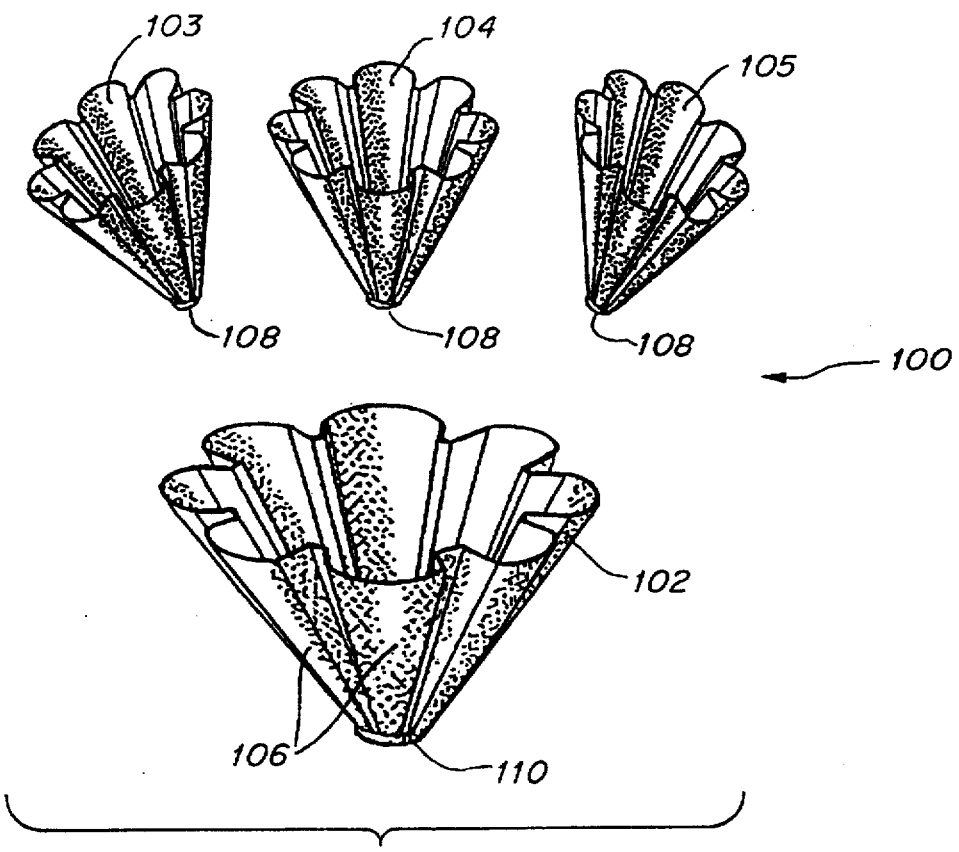
FIG. 2 is an exploded illustration of the enhanced implantable prosthesis of the present invention.
Figure 3:
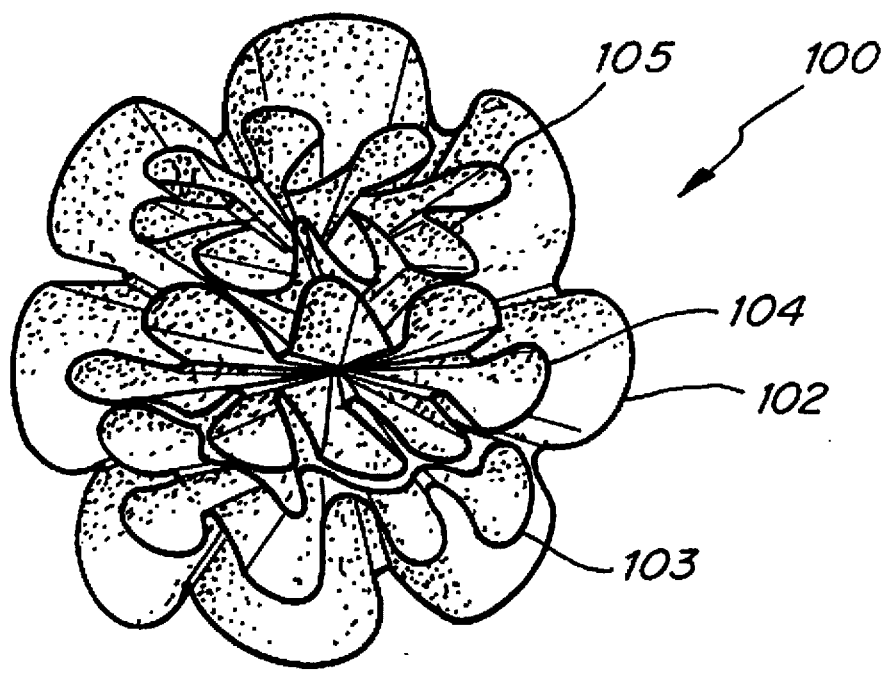
FIG. 3 is an illustration of an assembled implantable prosthesis according to the present invention.

The implantable prosthesis 100 for repairing tissue and muscle wall defects, illustrated in FIGS. 2–3, includes a flexible, hollow outer plug 102 which is compressible into a slender configuration that approximates the shape of the defect and at least two or more inner filler plugs 103–105, preferably three, which impart bulk to, and stiffen, the implant when it is confined within the tissue or muscle wall opening. The outer mesh body may be conical, as shown, and a portion or all of the surface of the outer plug may be pleated 106 to enhance the pliability and flexibility of the implant, allowing the prosthetic to conform to irregularities in the shape of the hernia without kinking or buckling. At least one, and preferably all, of the inner filler plugs may be smaller versions of the outer plug, having a conical shape, rounded tip, open base, longitudinal pleats and being radially compressible. The pleated surface of the inner plugs, and outward resilience, enhance the packing and stiffening affect of the mesh filling. The inner filler plugs may be positioned side-by-side along a transverse axis of the implant as illustrated, or may be arranged circumferentially, or in any other fashion as would provide the desired stiffness and bulkiness when the outer plug is seated within the constricting confines of the tissue or muscle wall rupture.

A relaxed and uncompressed outer plug, prior to insertion into a defect, is illustrated in FIG. 3 with the inner filler plugs arranged side-by-side so that there is at least one point of contact between the sidewalls of adjacent filler plugs and, preferably, at least one point of contact between the sidewalls of the outer plug and the inner plugs positioned thereagainst. The inner filler plugs may be partially flattened to make room for the other plugs. As shown, the plugs are pinched to such an extent that pleats on opposing sides lie in a common vertical plane. Although the inner filler plugs are illustrated as having the same size and shape, varying sizes and shapes of these components are contemplated so long as the mixture of plugs ultimately chosen enhances the packing of the outer plug. Thus, the inner plugs may have a conical, truncated conical or cylindrical shape, or other configuration, which may be partially compressed as other filler plugs are added to the outer plug cavity and which may become extensively reduced when the implantable prosthesis is placed within the tissue or muscle wall defect.

The inner filler plugs may be secured through their tips 108 to the atraumatic end 110 of the outer plug. This arrangement allows independent movement of each filler plug relative to the outer plug, and to each other, as the implant is compressed by the narrow tunneling walls of the hernia. Sidewall stitches, or other fastening mechanisms, may additionally be provided to secure at least the outermost of the filler plugs and the outer plug. These junctions restrain the inner filler bodies from protruding beyond the base of the outer plug when the implant is compressed, preventing the margin of the outer base, used to suture or staple the implant to neighboring tissue, from becoming obscured. Providing the inner filler bodies with a predetermined height that is shorter than the outer plug also ensures sufficient clearance for fixation of the outer plug base.

The outer plug and inner filler plugs are preferably formed of knitted polypropylene monofilament mesh fabric, such as Marlex® mesh. Other biologically compatible soft tissue reconstruction or repair materials, having openings for tissue ingrowth, are contemplated including, without limitation, Prolene®, Dacron®, Teflon® (expanded PTFE) and Merselene®. Although a single layer knitted monofilament fabric is preferred, the porous prosthetic repair material may alternatively be formed of multi filament yarns and woven, braided and extruded devices are considered within the scope of the invention as are multiple layer devices. The larger outer and smaller inner filler plugs preferably are formed by hot molding a circular sheet of mesh fabric into a cone or other desired plug shape. The cone is supported in a fixture having fins which project into the mesh plug for forming the rounded pleats. The prosthetic is heated and then cooled, forming a single layer plug with the desired shape and longitudinally pleated surface. In a representative embodiment, the implantable prosthesis for hernia repair and soft tissue reconstruction includes a conical outer plug formed of Marlex® knitted monofilament polypropylene mesh fabric having a height of 1.5 inches and a round base with a diameter of 2.0 inches and three inner filler plugs, also formed of Marlex® mesh, arranged side-by-side within the outer plug, and having a height of 1.1 inches and a preassembled diameter of 1.5 inches. When fixed within the outer plug, the base of the partially flattened inner filler plugs has a major axis diameter of 1.75 inches and a minor axis diameter of 0.375 inches. A clearance of 0.1875 inches is provided between the end of the filler plugs and the margin of the outer plug base.

The present invention therefore provides a prosthetic implant, amongst which are certain of the following advantages. The mesh device is compressible into varying shapes and sizes, allowing a single, or at most a nominal range of sizes, to be indicated for the repair of most commonly occurring inguinal defects and soft tissue reconstructions. The pleated surface allows the implant to conform to localized irregularities in the contours of the rupture. A relatively enhanced stiffening and bulking affect is provided by the filler plugs, allowing the prosthesis to be used in the repair of large defects.

It should be understood that the foregoing description of the invention is intended merely to be illustrative thereof and that other embodiments, modifications, and equivalents of the invention may be within the scope of the invention recited in the claims appended hereto. Consequently, although the invention has been described in connection with a conical outer plug and three conical inner filler plugs, the scope of the invention includes other shapes of outer and filler plugs and a greater or lesser member of filler plugs. While the outer and filler plugs may have rounded tips and pleated surfaces, the breadth of the invention covered hereby is not so limited. Further, the inner filler plugs may be constructed and arranged within the outer plug cavity so that they do not become compressed or flattened until the prosthesis is placed within a smaller defect opening.

We claim:

1. An implantable prosthesis for repairing or reconstructing a tissue or muscle wall defect, comprising:
   a flexible, hollow outer plug formed of a biologically compatible, implantable fabric having openings therein for tissue ingrowth, said hollow plug including a cavity therein and being compressible radially upon insertion into the defect; and
   at least two inner filler plugs pre-formed to include a sidewall defining a cavity in an uncompressed configuration, and being further formed of a biologically compatible, implantable fabric having openings therein for tissue ingrowth and positioned within said outer plug cavity which impart bulk to, and stiffen, said implantable prosthesis when said outer plug is compressed radially upon insertion into the defect.

2. The implantable prosthesis recited in claim 1 wherein said outer plug is compressible into a configuration which closely approximates the shape of the defect.

3. The implantable prosthesis recited in claim 1 wherein said outer plug further includes a pleated surface which is conformable to irregularities in the tissue or muscle wall defining the defect when said outer plug is compressed.

4. The implantable prosthesis recited in claim 1 wherein said outer plug is conical.

5. The implantable prosthesis recited in claim 1 wherein at least one of said at least two inner filler plugs is conical.

6. The implantable prosthesis recited in claim 1 wherein at least one of said at least two inner filler plugs includes a pleated surface in an uncompressed configuration.

7. The implantable prosthesis recited in claim 1 wherein said at least two inner filler plugs are moveable relative to one another.

8. The implantable prosthesis recited in claim 1 wherein said at least two inner filler plugs are moveable relative to said outer plug.

9. The implantable prosthesis recited in claim 1 wherein said outer plug includes a sidewall and at least one of said at least two inner filler plugs is secured to said sidewall.

10. The implantable prosthesis recited in claim 1 wherein said at least two inner filler plugs are shaped similarly to, but are smaller versions of, said outer plug.

11. The implantable prosthesis recited in claim 1 wherein said outer plug includes a tip, said at least two inner filler plugs include a tip, and said tips of said at least two inner filler plugs are attached to said tip of said outer plug.

12. The implantable prosthesis recited in claim 1 wherein said outer plug includes a fastening margin at one end thereof, and said inner filler plugs are constructed and arranged within said outer plug cavity so as not to obscure said fastening margin when said outer plug is compressed.

13. The implantable prosthesis recited in claim 1 wherein said at least two inner filler plugs are arranged side-by-side.

14. The implantable prosthesis recited in claim 1 wherein said outer plug and said at least two inner filler plugs each include a tip and a sidewall and wherein there is at least one point of contact between said sidewalls of adjacent of said at least two inner filler plugs and at least one point of contact between said sidewalls of said outer plug and said at least two inner filler plugs.

15. The implantable prosthesis recited in claim 1 wherein said at least two inner filler plugs includes three inner filler plugs.

16. An implantable prosthesis for repairing or reconstructing a tissue or muscle wall defect, comprising:

a flexible conical outer plug formed of a biologically compatible, implantable fabric having openings therein for tissue ingrowth, including an atraumatically configured end, an open base and a cavity therebetween, said conical outer plug being radially compressible upon insertion into the defect into a configuration which approximates the shape of the defect and including a pleated surface which allows said outer plug to conform to irregularities in the tissue or muscle wall defining the defect; and at least two flexible conical inner filler plugs, each formed of a biologically compatible, implantable fabric having openings therein for tissue ingrowth, said at least two flexible conical inner filler plugs including a pleated surface in an uncompressed configuration and being positioned within said outer plug cavity, whereby said at least two flexible conical inner filler plugs impart bulk to, and stiffen, said implantable prosthesis when said flexible conical outer plug is compressed upon insertion into the defect.

17. The implantable prosthesis recited in claim 16 wherein said at least two inner conical filler plugs are in a partially flattened configuration prior to radial compression of said outer plug.

18. The implantable prosthesis recited in claim 17 wherein said pleated surface on opposing sides of said at least two inner conical filler plugs lies in a common vertical plane prior to radial compression of said outer plug.

19. The implantable prosthesis recited in claim 16 wherein said at least two flexible conical inner filler plugs include a tip, an open base and a cavity therebetween.

20. The implantable prosthesis recited in claim 16 wherein said outer conical plug includes a margin and said at least two inner conical filler plugs are constructed and arranged within said outer plug cavity to provide clearance for said margin.

* * * * *